(12) United States Patent
Hemblade

(10) Patent No.: US 6,946,855 B1
(45) Date of Patent: Sep. 20, 2005

(54) ELECTRICAL RESISTANCE SENSOR AND APPARATUS FOR MONITORING CORROSION

(75) Inventor: Barry Hemblade, West Sussex (GB)

(73) Assignee: Cormon Limited, (GB)

( * ) Notice: Subject to any disclaimer, the term of this patent is extended or adjusted under 35 U.S.C. 154(b) by 0 days.

(21) Appl. No.: 09/980,806

(22) PCT Filed: Apr. 10, 2000

(86) PCT No.: PCT/GB00/01348

§ 371 (c)(1),
(2), (4) Date: Apr. 15, 2002

(87) PCT Pub. No.: WO00/63674

PCT Pub. Date: Oct. 26, 2000

(30) Foreign Application Priority Data

Apr. 19, 1999 (GB) .................................... 9908950

(51) Int. Cl.$^7$ ........................ G01R 27/08; G01N 27/00
(52) U.S. Cl. ...................................... 324/700; 324/71.2
(58) Field of Search ............................... 324/700, 699, 324/71.1–71.2, 706, 691; 202/404

(56) References Cited

U.S. PATENT DOCUMENTS

| | | | |
|---|---|---|---|
| 2,987,672 A | 6/1961 | Marsh et al. ................. | 324/71 |
| 3,155,933 A | 11/1964 | Rohrback et al. ............. | 338/13 |
| 3,821,642 A | 6/1974 | Seymour ..................... | 324/65 |
| 4,019,133 A | 4/1977 | Manley et al. ................ | 324/65 |
| 4,158,806 A * | 6/1979 | Kotylev et al. ............. | 324/700 |
| 4,338,097 A | 7/1982 | Turner et al. ................ | 23/230 |
| 4,338,563 A | 7/1982 | Rhoades et al. .............. | 324/65 |
| 4,426,618 A | 1/1984 | Ronchetti et al. ............. | 324/65 |
| 4,587,479 A | 5/1986 | Rhoades ...................... | 324/65 |
| 4,603,113 A | 7/1986 | Bauer ............................. | 436/6 |
| 4,703,253 A | 10/1987 | Strommen ................... | 324/65 |
| 4,703,254 A | 10/1987 | Strommen ................... | 324/65 |
| 5,036,287 A | 7/1991 | Serwatzky ................... | 324/700 |
| 5,243,297 A | 9/1993 | Perkins et al. .............. | 324/700 |
| 5,446,369 A | 8/1995 | Byrne et al. ................ | 324/71.2 |
| 5,583,426 A * | 12/1996 | Tiefnig ...................... | 324/71.2 |
| 5,854,557 A | 12/1998 | Tiefnig ........................ | 324/700 |

FOREIGN PATENT DOCUMENTS

| | | |
|---|---|---|
| EP | 0 150 552 | 5/1984 |
| WO | WO 86/02728 | 5/1986 |

* cited by examiner

Primary Examiner—Anjan Deb
Assistant Examiner—Amy He
(74) Attorney, Agent, or Firm—Westman, Champlin & Kelly

(57) ABSTRACT

An apparatus (1) is disclosed for monitoring the effect on a material of exposure to a fluid, and thereby monitoring the effect on a section of pipe (9) for carrying the fluid. The apparatus includes a sensor element (51) exposed to the fluid and formed as a ring of the material coaxially mounted within, but electrically insulated from, the section of pipe (9). Changes in the electrical resistance of the sensor element (51) are monitored. Preferably, the apparatus also includes a reference element (31) electrically insulated from the pipe (9), electrically connected in series to the sensor element (51) and protected from exposure to the fluid. The elements may both be made from the same material as the pipe (9) and, as they are contained within it, experience the same temperature and pressure variations as the pipe (9). In this manner a change in the resistance of the sensor element (51) caused by corrosion/erosion by the fluid accurately indicates the degree of corrosion/erosion of the pipe (9) carrying the fluid.

11 Claims, 3 Drawing Sheets

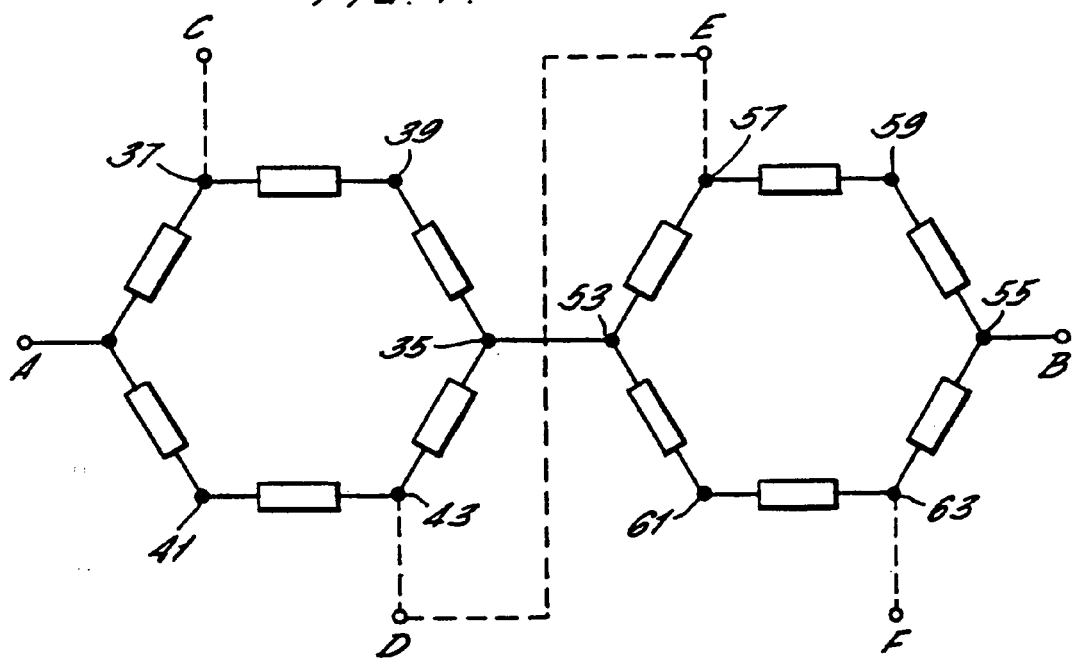
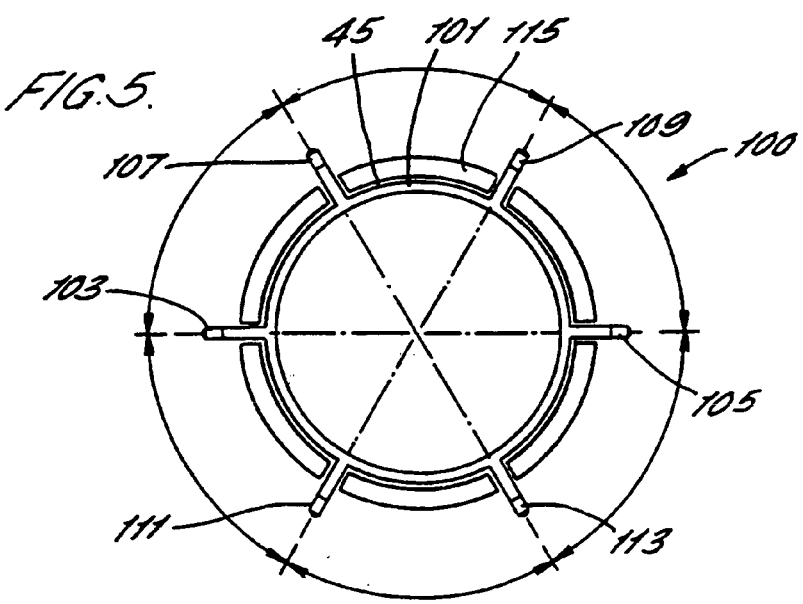

ELECTRICAL RESISTANCE SENSOR AND APPARATUS FOR MONITORING CORROSION

This application is a national stage filing under 35 U.S.C. § 371 and priority is hereby claimed on International Application No. PCT/GB00/01348, filed Apr. 10, 2000, which International Application was published in English as No. WO 00/63674.

FIELD OF THE INVENTION

The present invention relates to electrical resistance corrosion sensors for detecting and monitoring loss of material due to corrosion and/or erosion caused by the interaction of that material with its environment. More specifically, the present invention relates to electrical resistance corrosion sensors for monitoring corrosion and/or erosion of the internal surface of a pipe through which a fluid environment flows.

BACKGROUND OF THE PRIOR ART

Corrosion sensors are used in the detection and monitoring of loss of material, such as the internal surface of a pipeline wall, due to corrosion and/or erosion from interaction between the material and the environment in contact with the material. Such conditions exist in oil or gas pipelines.

Commonly, corrosion sensors use electrical resistance methods to detect loss of material due to corrosion/erosion. Such a corrosion detector system includes using the principles of electrical resistance to determine corrosion/erosion of a pipeline wall surface. Such a system consists of measuring the thickness of the pipeline wall with pick-up points along the external surface of a pipeline section. The pipeline section is energised by a longitudinal current applied at two points adjacent to either side of the pick-up area. The current density map through the material, proportional to wall thickness, is derived by measurement of voltages across the matrix of pick-up points relative to an external reference, and the resistive ratios are converted into the metal loss.

The sensitivity of such prior art corrosion detector arrangements is limited by various factors. For instance, the sensitivity of the corrosion detector arrangement is dependant on the maximum current which can be sustained. The maximum current is limited for intrinsically safe applications in potentially explosive environments such as in oil and gas pipelines. In such corrosion detector systems, sensitivity is also limited by the very small measured resistive voltages between array pick-up points. Disturbances such as noise and dc offsets occurring in the electronic circuitry of the corrosion detector systems and thermoelectric voltages and electromagnetic noise in the leads make high-resolution measurements of such small voltages difficult.

Additionally, changes in the temperature in the environment in which pipeline is situated changes the electrical resistance of the pipe. For example, the resistance of steel may change by 0.4% per ° C. In electrical resistance corrosion monitoring systems configured with an element having an exposed surface to the environment and a reference system external to the environment such as the pipeline fluid environment, changes in fluid temperatures significantly limit the accuracy and sensitivity of the monitoring system if the temperature of the pipeline and external reference system differ. To illustrate, a nominal difference in temperature of 0.25° C. between the pipeline and reference system will cause a change in the resistance ratio of 1000 ppm.

Furthermore, the circumferential and radial temperature excursions may be present around the profile of the pipeline. This will depend on the pipeline process fluid conditions and the location of the pipeline itself. For example, the fluid environment may comprise a cross-sectional layered profile of water, crude oil, and gas. The boundary phases between these layers may also change over time. A difference of 0.25° C. between the top and bottom of the pipeline would cause a further change in the resistance ratio of about 1000 ppm.

The hydrostatic and thermal stresses induced in pipeline structures will also influence the measured resistive voltages. In prior art corrosion detector arrangements with a reference system external to the fluid environment, the reference system will not be subjected to the hydrostatic and thermal loads and therefore further errors will occur.

The mechanisms involved in the change of resistance due to strain are extremely complex and not easily predicted. Change in resistance due to strain relates to the distortion of the lattice structure, which varies according to material composition and microstructures. Although the affects are much less than temperature, typical pipeline steels exhibit changes of between 2000–4000 ppm per 100 BAR of pressure or 20–40 ppm per BAR. Of course, in prior art corrosion monitoring with an external reference system, the external reference system is not subject to the changing internal pressure of the pipeline and the external reference system is not subject to the resultant changing resistive voltages. This contributes to further errors.

Similarly, as temperature change occurs there will be subsequent residual thermal stresses induced, resulting in further change in the resistive voltages. In addition, it is apparent that under a pressurised system the change in wall thickness due to corrosion and/or erosion will result in an increase in radial and circumferential stress distributions through the pipe wall. This will in turn induce further unwanted change to the measured resistive voltages.

The cumulative effect of resistive voltage changes due to changes of in process conditions not adequately compensated by the referencing system could result in expected deterioration of resolutions in excess±4000 ppm, for a temperature difference between pipeline and external reference system of 1° C. and a pressure difference of 100 BAR. With additional errors expected due to profile temperature and stress effects.

Therefore, there is a need for an electrical resistance corrosion monitor with a greater sensitivity to accurately measure at a higher resolution, the corrosion and/or erosion of a pipeline in a corrosive/erosive environment, especially where the environment temperature and/or hydrostatic pressure may be fluctuating.

SUMMARY OF THE INVENTION

The present invention provides apparatus for monitoring the effect on a material of exposure to a fluid, said apparatus comprising a sensor element formed as a ring of the material, wherein said ring is mounted coaxially in a section of pipe for carrying said fluid, so as to be exposed to said fluid, and is electrically insulated from said pipe, and means for monitoring changes in electrical resistance in said ring sensor element.

An embodiment of the invention provides the ability to measure the internal corrosion/erosion profile of an exposed sensor ring adjacent to a co-axially spaced electrically insulated reference ring whereby current injection is applied at diametrically opposite positions and measured voltages are a function of the circumferential position.

Embodiments of the sensor arrangement provide sensor elements that possess geometric, physical dimensional, metallurgical and dynamic similarity to that of the monitored pipeline. The ring sections may be formed from actual pipeline material to act as the corroding/eroding sensor ring exposed element and compensating reference ring. In this manner, the sensing exposed ring and reference ring possess virtually identical metallurgical and microstructural properties of the pipeline material influenced by material grade and fabrication process, and ensures identical potential corroding material and closely matching coefficients of resistivity, especially due to temperature and strain. The ability to subject the sensing and reference rings to substantially identical or similar pipeline process loading conditions that include changing environment temperatures, stresses including hydrostatic and thermal stress distributions, flow regimes including laminar/turbulent boundary layer effects/ heat transfer conditions, and the electrochemical environment, facilitate realistic simulation of the actual pipeline corrosion/erosion interface.

Embodiments of the invention further provide the ability to compensate for nominal and circumferential profile temperature and stress distribution effects by an in-situ adjacent co-axially spaced electrically insulated and corrosion/erosion protected reference ring to closely match the coefficients of resistance of the sensing and reference rings.

Another embodiment of the invention further provides a compound ring comprising two rings with an exposed ring mounted in and strengthened by a back-up ring with an electrically insulating barrier between the expose ring and the back-up ring. In this embodiment, the back-up ring provides structural support for the exposed ring, which may be relatively thinner than the reference element to provide additional resolution whilst maintaining required strength to the thinner exposed element.

DESCRIPTION OF THE DRAWINGS

Examples of embodiments of the present invention will now be described with reference to the drawings in which:—

FIG. 4 shows a block diagram of the electrical connection point configuration of the reference element and exposed element of an embodiment of the invention; and FIG. 5 shows a cross-sectional view of another embodiment of the sensor elements.

DETAILED DESCRIPTION

Figure 1:
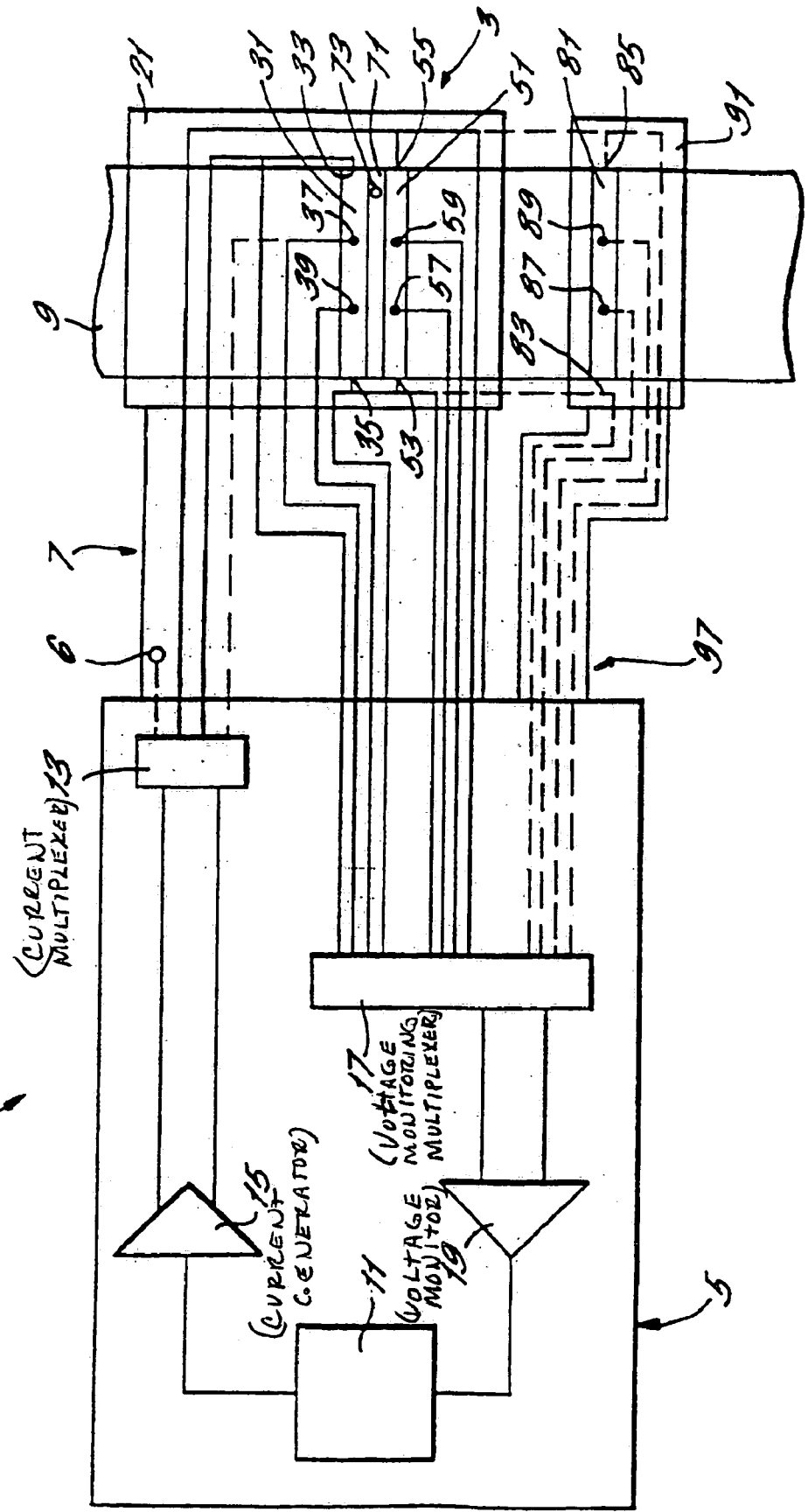
FIG. 1 shows a block circuit diagram of an embodiment of the invention.

A corrosion sensor 3, which is used in a corrosion monitoring system 1 for monitoring corrosion in an environment such as a pipeline 9, is shown in FIG. 1. The corrosion monitoring system 1 generally comprises a sensor assembly 3 comprising a housing 21 for a reference element 31 and an exposed element 51, electronic circuitry 5 and a cable 7 for connecting the electronic circuitry to the sensor assembly 3.

The exposed element and the reference element are electrically connected in series and connected to a current generator 11,15 which drives current through the series circuit. The elements are connected to the electronic circuitry at pick-off points, e.g. points 33,35,53,55. The points define two portions on each of the sensor elements for the current to flow through. The electronic circuitry further comprises voltage monitoring means 11,19 arranged to monitor the voltage developed across each of the regions defined by the points of the exposed and reference elements.

In preferred embodiments discussed in further detail below, the electronic circuitry further includes a current multiplexer 13 for alternately switching the current supplied to different points on the exposed and reference elements, and a voltage monitoring multiplexer 17 for switching the serial link electrically connecting the elements, and also for the voltage monitoring means to measure alternately the voltage across each element.

In an embodiment of the invention, each of the elements 31,51 of the sensor arrangement 3 have a closed-ring configuration. The reference closed-ring element 31 is electrically connected in series with the exposed closed-ring element 51. Conveniently, the sensor in any of the embodiments may be constructed to fit any pipeline that is to be monitored for corrosion/erosion. The exposed element and the reference element may be formed from adjacent sections or slices of the pipeline. This construction of the sensor elements ensures that the sensor elements are near to identical as possible including the material coefficient of resistivities. The process by which the slices are formed is preferably a process that minimises change to the microstructure of the material both local to and remote from the edges of the elements, and may for example include spark machining, wire corrosion, etching and the like. Each section or slice of the pipeline is preferably in the range of 8 mm–12 mm wide. The thickness of the elements 31,51 are determined by the dimensions of the pipeline.

Conveniently, of course, in embodiments of the invention the sensor elements may be formed from a material different than the material of the actual pipeline material. For example, if the corrosion/erosion effects from the pipeline environment are to be monitored for a material different to that of the material of the pipeline the corrosion sensor is mounted, then the sensor elements may be for example, formed from sections or slices of another pipeline of the material of interest. Of course, in this embodiment the pipeline that the sensor elements are formed from may have similar dimensions as the pipeline the sensor is to be mounted in.

Figure 2:
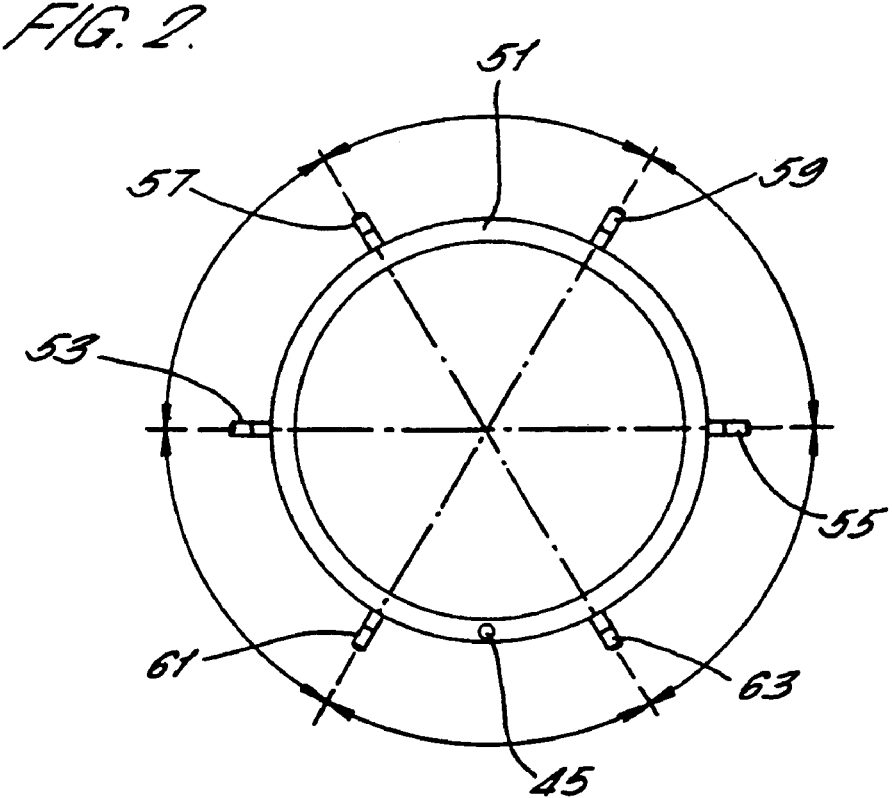
FIG. 2 shows a cross-sectional view of an exposed element of an embodiment of the invention.
Figure 3:
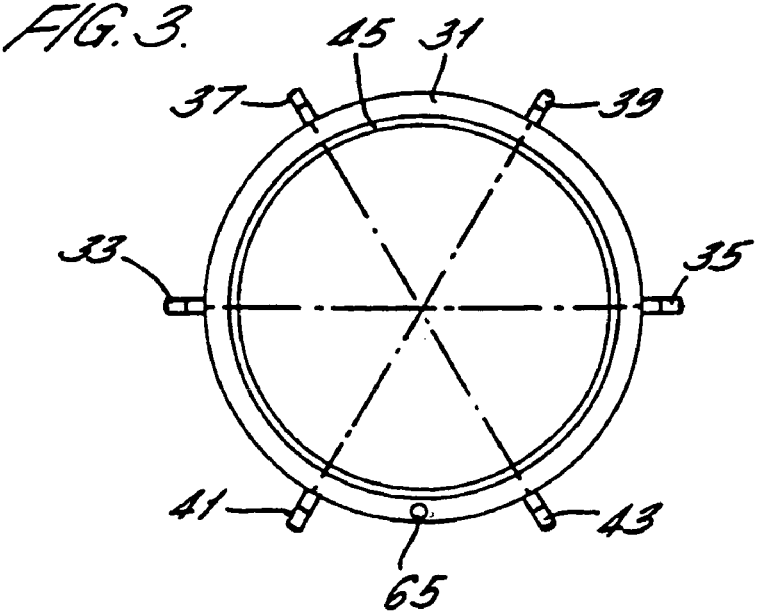
FIG. 3 shows a cross-sectional view of a reference element of an embodiment of the invention.

The elements maintain the radial orientation when mounted in the sensor. As shown in FIGS. 2 and 3, orientation marks 45,65 are provided on the elements which are aligned when mounted in the sensor 3. The orientation marks are made prior to parting of the elements from the pipeline material. The elements 31,51 are co-axially spaced and separated by a spacer ring 71. The spacer ring is coated with an insulating material such as epoxy resin or ceramic or the like. The material of spacer ring may form part of the housing 21 and the material of the spacer ring may also insulate the elements 31,51 from the pipeline when the sensor is mounted in the pipeline 9.

Each ring element 31,51 consists of additional co-planer pick-off points equally spaced around the outer circumference of the ring. The pick-off points are formed typically by spot welding, i.e. localised heat treatment to minimise any disturbance to the resistive properties of the elements. For example, each ring comprises four such points in addition to points 33,35,53,55 as discussed above for connecting the sensor elements to the electronic circuitry 5, however, embodiments of the invention do not necessarily require additional points and fewer or more than four additional points may be used.

The pick-off points in this example define three regions on each portion of each element. On the reference ring element 31 pick-off points 37,39 define three sectors on the upper portion of the reference element and pick-off points 41,43 define three sections on the lower portion of the reference element. Similarly, on the exposed ring element 51 pick-off points 57,59 define three sections on the upper portion of the exposed element and pick-off points 61,63 define three sectors on the lower portion of the exposed element. Of course, although six points on each of the elements are described with reference to this embodiment, any number of pick-off points may be used. The number of points chosen depends on the granularity of sectors required.

Referring to FIG. 4, a current input $I_{in1}$ is shown at a position A at pick-off point 33 of the reference ring element 31 and a current output $I_{out1}$ is shown at position B at pick-off point 55 of the reference ring element 51. In this arrangement, the elements are electrically connected at points 35 and 53 via multiplexer 17 for example, and position A and B of the elements are electrically connected to the current multiplexer 13.

A second current input $I_{in2}$ is shown at a position C at point 37 and a second current output $I_{out2}$ is shown at a position D at point 43 of the reference ring element. Similarly, a third current input $I_{in3}$ is shown at a position E at point 57 and a third current output $I_{out3}$ is shown at a position F at point 43 of the exposed ring element. In this arrangement, the ring elements are electrically connected as shown at position D and E from points 43 and 57 via multiplexer 17 for example, and the position C and B are electrically connected to the current multiplexer 13.

In this configuration, the current multiplexer 13 allows for selectively and alternately switching the current supplied to the different points A–B or C–F and simultaneously the multiplexer 17 for example may switch the linking points 35–53 or 43–57, respectively, on the exposed and reference elements and provides for a selectable dual position current generator which drives the current through the series circuit. The second current input position C is adjacent to a sector pick-off position A. Of course, other configurations may be provided having different current connecting points.

Similarly, in this embodiment, each of points 33,37,39, 35,41,47 of the reference element and each of points 53,57, 59,55,63,61 of the exposed element may be connected to the voltage monitoring multiplexer 17 for switching the voltage monitoring means to measure alternately the voltage across each sector defined by the points. The multiplexer is provided for switching the voltage monitoring positions across each ring and the voltages for each sector.

With reference to FIGS. 1 and 4, the operation of the sensor generally involves measuring the voltages across each sector on each of the elements, switching the drive current position and measuring the voltages with the new drive current position. In this configuration, there are six sectors on each ring, however, as discussed above, the number of sectors chosen may differ, i.e. more or fewer points may be selected. The resistance ratio of each sector is determined from the voltages developed across each sector. For the exposed element $R_s$, sector Ra is defined by points 53,57 which is indicated as 0°–60°, sector Rb is defined by points 57,59 which is indicated as 60°–120°, Rc is defined by points 59,55 which is indicated as 120°–180°, Rd is defined by points 55,63 which is indicated as 180°–240°, Re is defined by points 63,61 which is indicated as 240°–300°, and Rf is defined by points 61,53 which is indicated as 300°–360° of the exposed ring element. Sectors of the reference element are similarly identified, where sector $R_r$a is defined by points 33,37 indicated 0°–60°, sector $R_r$b is defined by points 37,39 indicated 60°–120°, $R_r$c is defined by points 39,35 indicated 120°–180°, $R_r$d is defined by points 35,43 indicated 180°–240°, $R_r$e is defined by points 43,41 indicated 240°–300°, and $R_r$f is defined by points 41,33 indicated 240°–300° of the reference ring element.

The ratio of resistance of the elements $R_s/R_r$ is first determined and the exposed element ratios Ra/Rb, Ra/Rc, Rf/Rd, Rf/Re are measured along with the reference element ratios $R_r$a/$R_r$b, $R_r$a/$R_r$c, $R_r$f/$R_r$d, $R_r$f/$R_r$e.

In this configuration the current multiplexer 13 then switches the drive current position switch to current input position C and current output position F. At this time, the points electrically linking the elements serially, are switched by multiplexer 17 for example from points 35,53 to points 43,57, as shown by a dashed line in FIG. 1, D–E. In this arrangement, the current input, current output, and the electrical connection between the elements rotates by 60 degrees.

The resistance ratios Ra/Rf and $R_r$a/$R_r$f are then measured. Both the element $R_r$, $R_s$, profiles may then be derived and profile in terms of Ra/Ra, Ra/Rb, Ra/Rc, Ra/Rd, Ra/Re and Ra/Rf, and $R_r$a/$R_r$a, $R_r$a/$R_r$b, $R_r$a/$R_r$c, $R_r$a/$R_r$d, $R_r$a/$R_r$e and $R_r$a/$R_r$f, respectively. Then, the $R_s$ profile is modified from the $R_r$ profile by the equation:

$$Ra/Rb=(T-xb)/(T-xa),$$

where T=ring thickness, xa=metal Loss in sector a, and x1+x2=2T(1−1/($R_s/R_r$)), where x1=effective metal loss of upper section of the ring element, x2=effective metal loss of lower section of the ring element. Similarly, the metal loss in each other sector may be determined. In an embodiment of the invention, a pressure sensor 73 that is commercially available may be positioned through an access hole in the spacer ring. In other embodiments the spacer ring 71 may also provide access for other monitoring devices such as electrochemical noise and linear polarisation resistance devices, and the like. For example, under typical load conditions, the pressure may be measured using the pressure sensor. Conveniently, the pressure readings, for example, may be used to calculate and eliminate changes caused by hydrostatic pressure effects.

In another embodiment, the sensor arrangement also provides the facility to monitor a number of independent sampled rings within one system, as shown in FIG. 1. An additional exposed element 81 is provided as part of the sensor 3. Additional element 81 may be formed in the same manner as the exposed element 51, as discussed above. The additional element 81 may comprise an additional housing 91 and cable 97 that electrically connects pick-off points, e.g. 83,87,89,85, to the voltage monitoring means multiplexer 17. Of course, the multiplexer 17 may also link the additional element 81 serially with the other elements in a similar manner as discussed above to provide a switching capability between linking points on the additional element linking to the other elements via the multiplexer. The additional element 81 enables comparative corrosion/erosion monitoring studies or trials of different materials or grades of material, such as welded sections, evaluation of new materials against existing materials, specially prepared or coated materials and the like. Additionally, the concurrent monitoring of identical samples is possible, thereby increasing data integrity, reliability and certainty.

In another embodiment, the sensor may comprise two or more pairs of reference and exposed elements. The pairs of elements may be electrically connected via multiplexing in a similar manner as discussed above. Providing an additional pair or pairs of reference element and exposed element allows for accurate corrosion/erosion monitoring. Thus, the number of pairs of rings is not limited to a single pair of rings.

In another embodiment of the sensor as shown in FIG. 5, the exposed element may be formed from two rings with an exposed ring 101 mounted in and strengthened by a back-up ring 115 with an electrically insulating barrier 45 between rings 115,101 to form a compound sensor ring 100. The compound ring exposed element 101 may be electrically connected in a similar manner to the reference element 31, as the exposed element 51 is electrically connected to the reference element 31, as discussed above, and the pick-off point elements may be electrically insulated from the back-up ring. The exposed element is preferably formed from the same material as the reference element, for example, adjacent slices or sections of a piece of pipeline. As discussed above, this ensures that the sensor elements possess substantially identical geometric, physical, metallurgical and dynamic similarities to each other as well as the pipeline. Of course, the elements do not necessarily need to be formed from the pipeline that the sensor will be mounted in, rather the elements may be formed from a pipeline of different a material, as discussed above. The back-up ring does not necessarily need to be the material of the pipeline and may be a material that provides greater strength for supporting the exposed element under fluid environment pressures and conditions. Additionally, if the back-up ring is of a material that is an electrically insulating material, the exposed ring and pick-off point elements may be in direct contact with the back-up ring.

In this embodiment, the back-up ring 115 provides structural support for the exposed ring, which may be relatively thinner than the reference element. In this embodiment the exposed element may have for example have any thickness that is less than thickness of the reference element. As the reference element and the exposed element are slices of the same pipeline, both share substantially the same thickness. Therefore, it is preferred to thin the element to a desired thickness by such means as wire erosion or spark erosion and the like. The compound ring may be formed by mounting within the reference element 31, where the elements may be formed from the same slice or section of pipeline and thinned with a layer of insulating material 45 separating the elements, however this may need further structural support. The exposed element 101 may be electrically connected together in series with the reference element 31, and both elements are electrically insulated from the pipeline, as described above. The back up element may be the reference element and the pick-off points on the exposed element 103,107,109,105,113,111 are radially aligned, coaxially adjacent and insulated from the points on the reference element. The points on the exposed element 101 are connected to the multiplexer and are each insulated from the reference element. As described above, connections are made to the current multiplexer 13 for switching the current through different points or portions as shown in FIG. 4, and the points linking the elements in series are connected via the multiplexer 17, for example. Embodiments of this two compound ring configuration provides additional resolution whilst maintaining required strength to the thinner exposed element.

Further modifications to the embodiments described herein will be apparent to those skilled in the art.

What is claimed is:

1. Apparatus for monitoring the effect on a material of exposure to a fluid, said apparatus comprising a sensor element formed as a closed ring of the material, wherein said ring is mounted coaxially in a section of pipe for carrying said fluid, so as to be exposed to said fluid, and is electrically insulated from said pipe, and a resistance monitor coupled to monitor changes in electrical resistance in said ring sensor element.

2. Apparatus as claimed in claim 1 further comprising a reference element, said reference element being formed also as a ring, mounted coaxially in said pipe section and insulated therefrom, said second ring element being protected from exposure to said fluid.

3. Apparatus as claimed in claim 2, wherein said sensor and reference elements each comprise at least one pair of diametrically opposed electrical connection points.

4. Apparatus as claimed in claim 3, wherein each of said elements comprises a predetermined number of pairs of diametrically opposed connection points, said connection points on each element being regularly spaced around the respective ring.

5. Apparatus as claimed in claim 4, wherein said sensor and reference element are connected in series by respective pairs of said diametrically opposed connection points, and said resistance monitor is arranged to determine the ratio of the resistances of said elements.

6. Apparatus as claimed in claim 5, wherein said resistance monitor is arranged to drive a current through said series connected elements and to pick off voltage values from the various connection points.

7. Apparatus as claimed in claim 6, wherein said resistance monitor is arranged to make at least one further set of measurements by reconnecting the elements in series by different pairs of diametrically opposed connection points, driving a current through the series connected elements and picking off a further set of voltage values from the various connection points.

8. Apparatus as claimed in claim 2, wherein said elements are coaxially spaced apart by a spacer ring.

9. Apparatus as claimed in claim 8, wherein said spacer ring comprises a pressure sensor.

10. Apparatus as claimed in claim 1, wherein at least said sensor element comprises a section cut from said pipe.

11. Apparatus for monitoring the effect on a material of exposure to a fluid, said apparatus comprising a sensor element formed as a closed ring of the material, wherein said ring is mounted coaxially in a section of pipe for carrying said fluid, so as to be exposed to said fluid, and is electrically insulated from said pipe, and a resistance monitor coupled to selectively monitor changes in electrical resistance in a plurality of sectors of said ring sensor element.

* * * * *